United States Patent [19]

Marhold et al.

[11] Patent Number: 4,600,787
[45] Date of Patent: Jul. 15, 1986

[54] PROCESS FOR THE PREPARATION OF AROMATIC COMPOUNDS WHICH CONTAIN PERFLUORINATED SIDE-CHAINS BONDED VIA A HETEROATOM

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 602,849

[22] Filed: Apr. 23, 1984

[30] Foreign Application Priority Data

Apr. 27, 1983 [DE] Fed. Rep. of Germany ....... 3315147

[51] Int. Cl.⁴ .................... C07D 319/14; C07C 51/00; C07C 43/20
[52] U.S. Cl. ................................ 549/362; 260/543 F; 260/543 R; 549/434; 568/649; 568/655
[58] Field of Search ..................... 549/380, 434, 362; 568/649, 655; 260/543 F, 543 R

[56] References Cited

U.S. PATENT DOCUMENTS

| | | | |
|---|---|---|---|
| 2,776,992 | 1/1957 | Gregory | 260/543 F |
| 3,219,690 | 11/1965 | Sheppard | 260/543 F |
| 4,110,345 | 8/1978 | Berkelhammer et al. | 549/434 |
| 4,157,344 | 6/1979 | Feiring | 568/588 |
| 4,377,711 | 3/1983 | Rico et al. | 568/649 |
| 4,438,275 | 3/1984 | Lantzsch et al. | 549/434 |
| 4,496,750 | 1/1985 | Anderson et al. | 549/455 |

FOREIGN PATENT DOCUMENTS 2329625  5/1977  France .

OTHER PUBLICATIONS

Sheppard, Journ. Amer. Chem. Soc. 83, pp. 4860–4861, (1961).

The Journal of Organic Chemistry, Band 44, Nr. 16, Aug. 3, 1979, Seiten 2907–2910; H. O. House et al.: "Enones With Strained Double Bonds. 2. the bicyclo [4.3.1] decane System".

*Primary Examiner*—Ethel G. Love
*Attorney, Agent, or Firm*—Sprung, Horn, Kramer & Woods

[57] ABSTRACT

Aromatic compounds which contain perfluorinated side-chains bonded via a heteroatom are prepared by treating aromatic compounds, which contain side-chains which are perhalogenated, but only partially fluorinated, and bonded via heteroatom, with a catalyst capable of transferring halogen atoms.

16 Claims, No Drawings

PROCESS FOR THE PREPARATION OF AROMATIC COMPOUNDS WHICH CONTAIN PERFLUORINATED SIDE-CHAINS BONDED VIA A HETEROATOM

The present invention relates to a process for the preparation of aromatic compounds, which contain perfluorinated side-chains bonded via a heteroatom, from aromatic compounds, which contain side-chains which are perhalogenated, but only partially fluorinated, and bonded via a heteroatom, by treatment with a catalyst.

Aromatic compounds which contain perfluorinated side-chains bonded via a heteroatom are important intermediate products for the preparation of herbicides (see DE-OS (German Published Specification) No. 2,848,531) and insecticides (see DE-OS (German Published Specification) No. 2,837,524 and DE-OS (German Published Specification) No. 3,023,328).

It is known that aromatic compounds which contain perfluorinated side-chains bonded via a heteroatom can be prepared by reacting the corresponding perchlorinated compounds with hydrogen fluoride. The disadvantage of this process is that, in general, an excess of hydrogen fluoride has to be employed, and this can be recovered only with difficulty, or has to be destroyed. A further disadvantage is that any other groups present which can be fluorinated, for example acid chloride groups, are also fluorinated; in general, this is undesirable and implies an additional consumption of hydrogen fluoride. Thus, for example, DE-OS (German Published Specification) No. 2,117,650 discloses that, depending on the way in which the reaction is carried out, the fluorination of 4-trichloromethoxybenzoyl chloride with hydrogen fluoride gives 4-trifluoromethoxybenzoyl fluoride and/or 4-difluorochloromethoxybenzoyl fluoride, but not 4-trifluoromethoxybenozyl chloride.

A process for the preparation of aromatic compounds which contain perfluorinated side-chains bonded via a heteroatom has now been found, which is characterised in that aromatic compounds, which contain side-chains which are perhalogenated, but only partially fluorinated, and bonded via a heteroatom, are treated with a catalyst capable of transferring halogen atoms.

In the process according to the invention, it is possible to employ the most diverse aromatic compounds which contain side-chains which are perhalogenated, but only partially fluorinated, and bonded via a heteroatom. These aromatic compounds can contain further substituents, for example alkyl, aryl, fluoroformyl, chloroformyl, nitro, chlorosulphonyl, cyano, 0-alkyl, 0-aryl and/or halogen groups. It is possible for one such substituent to be present or, independently of one another, for several, for example 2 to 4, identical or different substituents of this type to be present. The aromatic compounds can also be substituted by a carbocyclic ring.

The aromatic compounds can contain, per molecule, one or more of the side-chains which are perhalogenated but only partially fluorinated. These side-chains can also be present as a cyclic structure. This is then preferably bonded to the aromatic nucleus via two heteroatoms. The side-chains which are perhalogenated but only partially fluorinated preferably contain 1 or 2 atoms and, as halogens, and in addition to fluorine, preferably chlorine and/or bromine.

Examples of suitable heteroatoms, via which side-chains which are perhalogenated but only partially fluorinated are bonded to the aromatic nucleus, are oxygen, sulphur and/or nitrogen atoms.

A preferred group of compounds which can be employed in the process according to the invention are those of the formula

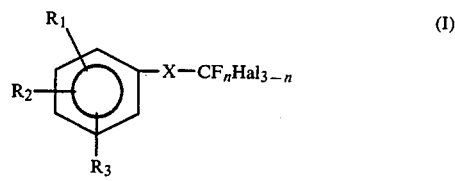 (I)

in which, independently of one another,
$R_1$ represents hydrogen, $C_1C_4$-alkyl, $C_6$–$C_8$-aryl, COF, COCl, $NO_2$, $SO_2Cl$, CN, 0-$C_1$–$C_4$-alkyl, 0-$C_6$–$C_8$-aryl, F, Cl or Br,
$R_2$ represents hydrogen, $NO_2$, $SO_2Cl$, F, Cl or Br,
$R_3$ represents hydrogen, COF, COCl, F, Cl or Br, or
$R_1$ and $R_3$ together represent a carbocyclic ring having 3 or 4 C atoms,
X represents 0, S or N-$C_1$–$C_4$-alkyl,
n represents 1 or 2 and
Hal represents Cl and/or Br.

Another preferred group of compounds which can be employed in the process according to the invention are those of the formula

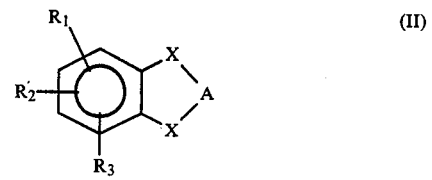 (II)

in which
$R_1$, $R_2$, $R_3$ and X have the meaning given in formula (I) and
A represents CFHal, $C_2FHal_3$, $C_2F_2Hal_2$ or $C_2F_3Hal$, wherein Hal represents Cl and/or Br.

Compounds which are particularly preferably employed in the process according to the invention are 2-fluoro-2-chloro-benzodioxole, 3-difluorochloromethoxybenzoyl fluoride, 2-difluoromethoxy-trichloromethoxybenzene, 6-nitro-2-chloro-2,3,3-trifluoro-benzo-1,4-dioxene, 4-difluorochloromethoxy-nitrobenzene, 3-difluorochloromethoxy-nitrobenzene, 4-difluorochloromethoxy-3-methylnitrobenzene, 4-difluorochloromethoxy-chloroformylbenzene, 3-difluorochloromethoxy-2,4-dichlorotoluene, 3-difluorochloromethoxy-4,6-dichlorotoluene, 3-difluorochloromethoxy-2,4,6-trichlorotoluene and 2-chloro-2,3,3-trifluoro-benzo-1,4-dioxene.

The aromatic compounds which are to be used in the process according to the invention and which contain side-chains which are perhalogenated, but only partially fluorinated, and bonded via a heteroatom can be obtained, for example, in a simple manner, by fluorination of the corresponding compounds which are perhalogenated but fluorine-free. The fluorination can be carried out, for example, using hydrogen fluoride or alkali metal fluorides. Since hydrogen fluoride is in general capable of replacing all halogen atoms present by fluorine atoms, special measures have to be taken in the fluorination with hydrogen fluoride in order to obtain compounds having a side-chain which is only partially fluorinated. Alkali metal fluorides are in general only capable of replacing some of the halogen atoms present by fluorine atoms. For this reason, the fluorination of aromatic compounds which contain side-chains which are perhalogenated but fluorine-free and bonded via a heteroatom is preferably carried out using alkali metal fluorides.

Examples of catalysts which are capable of transferring halogen atoms and are suitable for the process according to the invention are Lewic acids, in particular the halides of the elements boron, aluminium, tin, arsenic, antimony, titanium, molybdenum and iron. The fluorides, chlorides and bromides of these elements are preferred. Aluminium trichloride, aluminium tribromide, boron trichloride, boron trifluoride, arsenic pentachloride, antimony pentachloride, molybdenum pentachloride, titanium tetrachloride and iron trichloride are particularly preferred. If aluminium chloride is used as the catalyst, this is preferably used as a mixture with sodium chloride.

The catalysts can be employed, for example, in amounts of 0.001 to 0.1 mol per mol of aromatic compound. It is preferable to use 0.005 to 0.05 mol of catalyst, based on the aromatic compound.

The treatment with the catalyst can be carried out, for example, at temperatures in the range from 0° to 150° C. Temperatures in the range from 20° to 140° C. are preferred.

The reaction time can be, for example, in the range from 5 to 600 minutes. In general, reaction times between 30 and 200 minutes are sufficient.

The process according to the invention is carried out in general without solvents and diluents. However, it is also possible to carry out the process in the presence of solvents which are inert with respect to the catalysts. Examples of suitable solvents are chlorobenzene and dichlorobenzene.

Since, as a rule, the catalysts are sensitive to water, it is advantageous to carry out the process according to the invention substantially or completely in the absence of moisture.

The process according to the invention is carried out in general under atmospheric pressure, but it can also be carried out under reduced or elevated pressure. Reduced pressures are of advantage, for example, when relatively high-boiling aromatic compounds containing perfluorinated side-chains bonded via a heteroatom are prepared, and it is desired to remove these continuously during the reaction by distillation. Elevated pressures are of advantage, for example, when the boiling point of a component of the reaction mixture is lower, under atmospheric pressure, than the desired reaction temperature.

The process according to the invention can be illustrated by the following equations, using two selected examples:

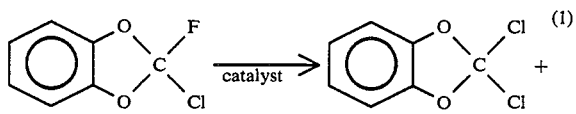
(1)

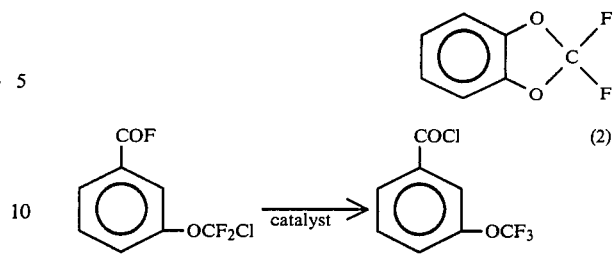
(2)

After the process according to the invention has been carried out, in general a mixture is obtained which contains, as component A, the resulting aromatic compound containing perfluorinated side-chains bonded via heteroatoms, and, as component(s) B, the corresponding aromatic compound containing perhalogenated, fluoride-free side-chains bonded via heteroatoms and/or aromatic compound(s) which have a lower fluorine content than the starting compound, and where relevant, as component(s) C, solvents, unreacted starting compound and/or by-products.

The process involves halogen interchange transfer in one or more fluoro-halo substituents bound to the aromatic nucleus via a hetero atom.

These mixtures can be worked up, for example, by distillation. Component A has in general the lowest boiling point, so this can be separated off first, while the process according to the invention is being carried out or after it has been carried out. If a solvent which boils below component A has been employed, this solvent has to be removed before component A is separated off by distillation. In general, it is advantageous if, in addition, the component(s) B and, where these are present, unreacted starting compounds are separated off by distillation from the residue present after component A has been separated off. The isolated component(s) B, after fluorination, for example by means of alkali metal fluorides, and the unreacted starting compounds which have been separated off can be added directly to another batch for carrying out the process according to the invention.

If the starting material for the process according to the invention contains fluorine atoms other than the fluorine atoms present in the partially fluorinated sidechains, for example where 3-difluorochloromethoxybenzoyl fluoride is used, reaction mixtures are frequently obtained which do not contain any component B but in addition to the desired end product (component A) which is 3-trifluoromethoxybenzoyl chloride where 3-difluorochloromethoxy-benzoyl fluoride is used, contain only any unreacted starting material and possibly small amounts of by-products, if indeed any additional substances are present at all. In such cases, working up is particularly simple, since, after component A has been separated off by distillation, the residue can be discarded or added to another batch for carrying out the process according to the invention.

In many cases, it is advantageous to remove component A continuously from the reaction mixture during the reaction, by distillation.

The catalysts employed are generally less volatile than the components A and B. They therefore generally remain in the residue during working up by distillation, and, together with this residue, can either be added to a further batch for carrying out the process according to the invention, or be discarded. In cases in which the catalyst employed, because of its volatility, would be troublesome during working up by distillation, it is advisable to decompose the catalyst before the distillation by adding a small amount of water.

It is decidedly surprising that, using the process according to the invention, it is possible to obtain good yields of aromatic compounds containing perfluorinated side-chains bonded via a heteroatom, since, in the preparation of these compounds by fluorination with hydrogen fluoride, the yields are low and large amounts of resinous by-products are obtained which cannot be utilised. In contrast, in the process according to the invention, only a small amount of resinous products, if any, are formed, and unreacted starting material and/or by-products having a low fluorine content or non-fluorinated by-products (the latter after subsequent fluorination) can be added to a further batch for carrying out the process according to the invention. In this context see, for example, Examples 8 and 9.

The examples which follow illustrate the process according to the invention without in any way restricting it.

EXAMPLES

EXAMPLE 1

(Preparation of the starting material 2-fluoro-2-chlorbenzodioxole, not according to the invention)

40 g of potassium fluoride, which had been dried at 400° C. beforehand, and 150 ml of dry acetonitrile were initially introduced into a dry stirred apparatus provided with a reflux condenser and a drying tube. 100 g (0.52 mol) of 2,2-dichlorobenzodioxole were added dropwise to this mixture at room temperature, and the mixture was then heated at the boil, under reflux, for 2 hours. It was then cooled, the solid constituents of the reaction mixture were filtered off under suction and the filtrate was fractionally distilled. 76 g (=91% of theory) of 2-fluoro-2-chlorobenzodioxole having a boiling point of 67° to 70° C. at 20 mbar and a refractive index $n_D^{20}$ of 1.4920 were obtained.

EXAMPLE 2

87 g (0.5 mol) of the 2-fluoro-2-chloro-benzodioxole prepared according to Example 1 were initially introduced into a stirred apparatus provided with a column and a reflux separator, 1 ml of antimony pentachloride was added and the mixture was heated to 100° C. for 5 hours. Thereafter, the bottom temperature was increased, and the 2,2-difluorobenzodioxole formed was distilled off over the column. 38 g of 2,2-difluorobenzodioxole having a boiling point of 130° to 131° C. at 1030 mbar and a refractive index $n_D^{20}$ of 1.4430 were obtained. The bottom product consisted predominantly of 2,2-dichlorobenzodioxole, which likewise was obtained by distillation. Gas chromatographic analysis of the reaction mixture before the distillation indicated that this mixture contained virtually only the two reaction products and that starting material was no longer present.

EXAMPLE 3

50 g of 3-difluorochloro-methoxybenzoyl chloride were initially taken in a stirred apparatus, and 0.5 ml of antimony pentachloride was added. Thereafter, the mixture was stirred for 3 hours at 100° C. and in the absence of moisture, and cooled, and the degree of conversion was determined by $F^{19}$-NMR spectroscopy. According to this, a mixture of 88% by weight of 3-trifluoromethoxy-benzoyl chloride and 12% by weight of starting material was present. Working up by distillation gave 37.5 g of pure 3-trifluoromethoxy-benzoyl chloride having a boiling point of 75° C. under 13 mbar.

EXAMPLE 4

30 g of 2-difluoromethoxy-trichloromethoxy-benzene were initially introduced into a dry stirred apparatus, and 1 ml of antimony pentachloride was added. A slightly exothermic reaction began. Thereafter, the mixture was stirred for 4 hours at 80° C. According to gas chromatographic analysis, the reacton mixture then contained 35% by weight of 2-difluoromethoxy-trifluoromethoxy-benzene and 6% by weight of 2-dichloromethoxy-trifluoromethoxy-benzene, in addition to compounds with a higher chlorine content. 7.2 g of 2-difluoromethoxy-trifluoromethoxy-benzene were separated off from the reaction mixture by distillation (boiling point: 88° to 89° C. under 200 mbar).

EXAMPLE 5

3 drops of antimony pentachloride were added to 50 g of 6-nitro-2-chloro-2,3,3-trifluoro-benzo-1,4-dioxene, and the mixture was then heated to 140° C. for 3 hours in the absence of moisture. Gas chromatographic analysis of the reaction mixture then indicates a content of 24.8% by weight of 6-nitro-2,2,3,3-tetrafluoro-benzo-1,4-dioxene in addition to 51.2% by weight of starting material and 23.2% by weight of 6-nitro-dichloro-difluoro-benzo-1,4-dioxene. 9.7 g of 6-nitro-2,2,3,3-tetrafluoro-benzo-1,4-dioxene having a boiling point of 110° to 112° C. under 18 mbar and a refractive index $n_D^{20}$ of 1.4750 were separated off from the reaction mixture.

EXAMPLE 6

60 g of 2-methyl-5-nitrophenylthio-chlorodifluoromethane were heated to 90° C. for 5 hours with 2 drops of antimony pentachloride. Thereafter, 23 g of 2-methyl-5-nitrophenylthio-trifluoromethane having a boiling point of 120° C. under 20 mbar and a refractive index $N_D^{20}$ of 1.5205 were separated off from the reaction mixture by distillation. The distillation residue contained, in addition to a small amount of starting material, mainly the dichlorofluoromethylthioether.

EXAMPLE 7

50 g of 2,4-dichlorophenyl chlorodifluoromethyl ether were added to a mixture of 2 g of aluminium chloride and 1 g of sodium chloride, and the mixture was heated to 120° C. for 2 hours. Gas chromatographic analysis showed that the reaction mixture then contained 34.4% of 2,4-dichlorophenyl trifluoromethyl ether and 25.5% of unreacted starting material.

EXAMPLE 8

200 g of 2-chloro-2,3,3-trifluoro-benzo-1,4-dioxene, 2.9 g of sodium chloride and 6.6 g of aluminium chloride were initially introduced into a stirred apparatus which was provided with an internal thermometer and a column filled with Wilson spirals and having a reflux separator, and the mixture was heated to an internal temperature of 180° to 205° C. The 1st fraction, having a boiling point of 145° to 158° C. under atmospheric pressure and a refractive index $n_D^{20}$ of 1.4295, was taken off at the top of the column in an amount of 108 g. Then, a 2nd fraction essentially consisting of starting material was obtained, and thereafter, under reduced pressure, a 3rd fraction essentially consisting of 2,2-dichloro-3,3-difluoro-benzo-1,4-dioxene ($n_D^{20}$: 1.4990) was obtained at 93° to 94° C. and 20 mbar. The 1st fraction was distilled again, and 76 g of tetrafluorobenzodioxene having a refractive index of 1.4220 were obtained at 144° to 147° C. and 1030 mbar.

EXAMPLE 9 (FOR COMPARISON)

In a fluorination apparatus, 500 g of hydrogen fluoride, 5 ml of antimony pentachloride and 150 g of 2-chloro-2,3,3-trifluoro-benzo-1,4-dioxene were heated to 140° C. for 6 hours. Thereafter, excess hydrogen flouride was removed by distillation, and the residue was subjected to fractional distillation. 27 g of 2,2,3,3-tetrafluorobenzo-1,4-dioxene having a boiling point of 142° to 146° C. were obtained. The residue consisted of a resinous mass. It was no longer possible to isolate any starting material.

What is claimed is:

1. A process for the preparation of an aromatic compound which contains a perfluorinated side-chain bound to the aromatic nucleus via a heteroatom which comprises contacting an aromatic compound containing a perhalogenated side-chain which is only partially fluorinated and which is bound to the aromatic nucleus via a heteroatom with a catalyst, said compound which is perhalogenated, but only partially fluorinated having the formula

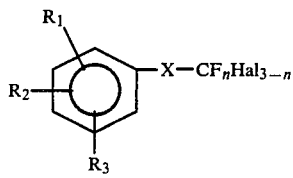

in which independently of one another,

R$_1$ represents hydrogen, C$_1$-C$_2$-alkyl, C$_6$-C$_8$-aryl, COF, COCl, NO$_2$, SO$_2$Cl, CN, 0-C$_1$-C$_4$-alkyl, 0-C$_6$-C$_8$-aryl, F, Cl or Br, R$_2$ represents hydrogen, NO$_2$, SO$_2$Cl, F, Cl or Br, R$_3$ represents hydrogen, COF, COCl, F, Cl or Br, or R$_1$ and R$_3$ together represent a carbocyclic ring having 3 or 4 C atoms, X represents O or S, n represents 1 or 2 and Hal represents Cl and/or Br, said catalyst being selected from the group consisting of aluminum trichloride, aluminum tribromide, boron trichloride, arsenic pentachloride, antimony pentachloride, molybdenum pentachloride, titanium tetrachloride, iron trichloride and mixtures thereof, said catalyst being present in an amount of 0.001 to 0.1 mol per mol of aromatic compound, which is perhalogenated, but only partially fluorinated, wherein such process involves halogen interchange transfer in one or more fluoro-halo substituents bound to the aromatic nucleus via a hetero atom.

2. A process according to claim 1, wherein the aromatic compound which is perhalogenated but is only partially fluorinated contains an alkyl, aryl, fluoroformyl, chloroformyl, nitro, chlorosulphonyl, cyano, alkoxy, aryloxy and/or halogen atom.

3. A process according to claim 1, wherein the said aromatic compound which is perhalogenated but only partially fluorinated is substituted with a carbocyclic ring.

4. A process according to claim 1, wherein the said aromatic compound which is perhalogenated but only partially fluorinated is in the form of a cyclic structure.

5. A process according to claim 1, wherein the said compound which is perhalogenated but only partially fluorinated has the formula

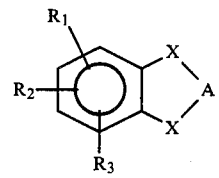

in which

R$_1$, R$_2$ R$_3$ and X have the meaning given in formula (I) and

A represents CFHal, C$_2$FHal$_3$, C$_2$F$_2$Hal$_2$ or C$_2$F$_3$Hal, wherein Hal represents Cl and/or Br.

6. A process according to claim 1, wherein the process is carried out at a temperature of 0° to 150° C.

7. A process according to claim 1, wherein the process is carried out in the absence of moisture.

8. A process according to claim 1, wherein the reaction mixture is worked up by distillation.

9. A process according to claim 1, wherein said compound which is perhalogenated but only partially fluorinated is 2-fluoro-2-chlorobenzodioxole.

10. A process according to claim 1, wherein said compound which is perhalogenated but only partially fluorinated is 3-difluorochloromethoxy-benzoyl fluoride.

11. A process according to claim 1, wherein said aromatic compound which is perhalogenated but only partially fluorinated is 2-fluoromethoxy-trichloromethoxy-benzene.

12. A process according to claim 1, wherein said compound which is perhalogenated but only partially fluorinated is 6-nitro-2-chloro-2,3,3-trifluoro-benzo-1,4-dioxene.

13. A process according to claim 1, wherein the said catalyst is selected from the group consisting of antimony pentachloride and aluminum chloride.

14. A process according to claim 1, wherein the catalyst is present in an amount of 0.005 to 0.05 mol per mol of aromatic compound.

15. A process according to claim 1, wherein the process is carried out at a temperature of 20° C. to 140° C.

16. A process according to claim 1, wherein the aromatic compound is selected from the group consisting of
2-fluoro-2-chloro-benzodioxole,
3-difluorochloromethoxy-benzoyl fluoride,
2-difluoromethoxy-trichloromethoxybenzene,
6-nitro-2-chloro-2,3,3-trifluoro-benzo-1,4-dioxene,
4-difluorochloromethoxy-nitrobenzene,
3-difluorochloromethoxy-nitrobenzene,
4-difluorochloromethoxy-3-methyl-nitrobenzene,
4-difluorochloromethoxy-chloroformylbenzene,
3-difluorochloromethoxy-2,4-dichlorotoluene,
3-difluoro-chloromethoxy-4,6-dichlorotoluene,
3-difluorochloromethoxy-2,4,6-trichlorotoluene and
2,chloro-2,3,3-trifluoro-benzo-1,4-dioxene.

* * * * *